United States Patent [19]

Ueda

[11] 4,427,000
[45] Jan. 24, 1984

[54] ENDOSCOPE HAVING A TEMPERATURE SENSITIVE MEMORY ALLOY PLATE AS THE TREATMENT INSTRUMENT DRIVING DEVICE

[75] Inventor: Yasuhiro Ueda, Kokubunji, Japan

[73] Assignee: Olympus Optical Co., Ltd., Tokyo, Japan

[21] Appl. No.: 393,817

[22] Filed: Jun. 30, 1982

[30] Foreign Application Priority Data

Jul. 13, 1981 [JP] Japan ................................ 56-109036

[51] Int. Cl.³ .............................................. A61B 1/06
[52] U.S. Cl. ...................................................... 128/6
[58] Field of Search .......................... 128/4–8

[56] References Cited

U.S. PATENT DOCUMENTS 4,182,547  1/1980  Siegmund ............................... 128/4
4,190,041  2/1980  Chikama ................................ 128/4

FOREIGN PATENT DOCUMENTS 56-54466  7/1981  Japan .

Primary Examiner—Kyle L. Howell
Assistant Examiner—Max F. Hindenburg

[57] ABSTRACT

An endoscope having a forceps raiser for raising up a treatment instrument, i.e., forceps, which is composed of a shape memory alloy plate varying in shape in accordance with temperature. A power source is connected to the shape memory alloy plate to supply a current to the shape memory alloy plate, thereby heating the shape memory alloy plate, and the shape memory alloy plate, i.e., the forceps raiser is varied in shape to raise the forceps.

7 Claims, 7 Drawing Figures

ENDOSCOPE HAVING A TEMPERATURE SENSITIVE MEMORY ALLOY PLATE AS THE TREATMENT INSTRUMENT DRIVING DEVICE

BACKGROUND OF THE INVENTION

The present invention relates to a treatment instrument driving device for altering the direction of a treatment instrument, e.g., forceps to be guided to a body cavity through the channel of an endoscope.

The endoscope has been used not only for observation or the photographing of the interior of a body cavity from the exterior, but also for the collection of the pathological tissue in the body cavity by forceps or the therapy of the tissue with a simple operation implement. For that purpose, a treatment instrument driving device for moving forceps or an operation implement to be guided into a body cavity through the channel of an endoscope to an objective position has become an important factor in the endoscope.

According to a conventional treatment instrument driving device, a driving member is arranged in a distal closet provided at the distal portion of an endoscope, being pivotally secured at its one end to the distal portion, and engaged at its other end to an operation wire inserted into the guide tube of the endoscope. The driving member thus rises when the operation wire is pulled, and forceps are then moved to a predetermined position according to the rising angle of the operation wire. With such a structure, a gap is produced between the operation wire and the guide tube, and the gap is exposed with the distal closet. Therefore, a contaminated solid or liquid is feasibly introduced into the gap. The contaminated solid or liquid thus accumulated in the gap not only prevents the rising of the driving member due to the operation wire, but is also unsanitary. Further, the treatment instrument driving device is used in the very narrow position of the endoscope. Accordingly, a problem occurs in the cleaning treatment of the narrow position after use.

SUMMARY OF THE INVENTION

It is an object of the present invention to provide a treatment instrument driving device which can be provided in the distal closet of an endoscope without a gap, and which is sanitary with good operability.

According to the present invention, a driving member, i.e., forceps raiser of a treatment instrument driving device, formed, for example, of a shape memory alloy, is installed so as not to produce a gap in the distal closet of an endoscope. An electric current is thus supplied to the forceps raiser to vary the temperature thereof. The forceps raiser is heated due to the current supply, and is thereby deformed. As a result, the forceps are displaced by the forceps raiser.

DETAILED DESCRIPTION OF THE PREFERRED EMBODIMENTS

The present invention will now be described in more detail with reference to the accompanying drawings.

Figure 1:
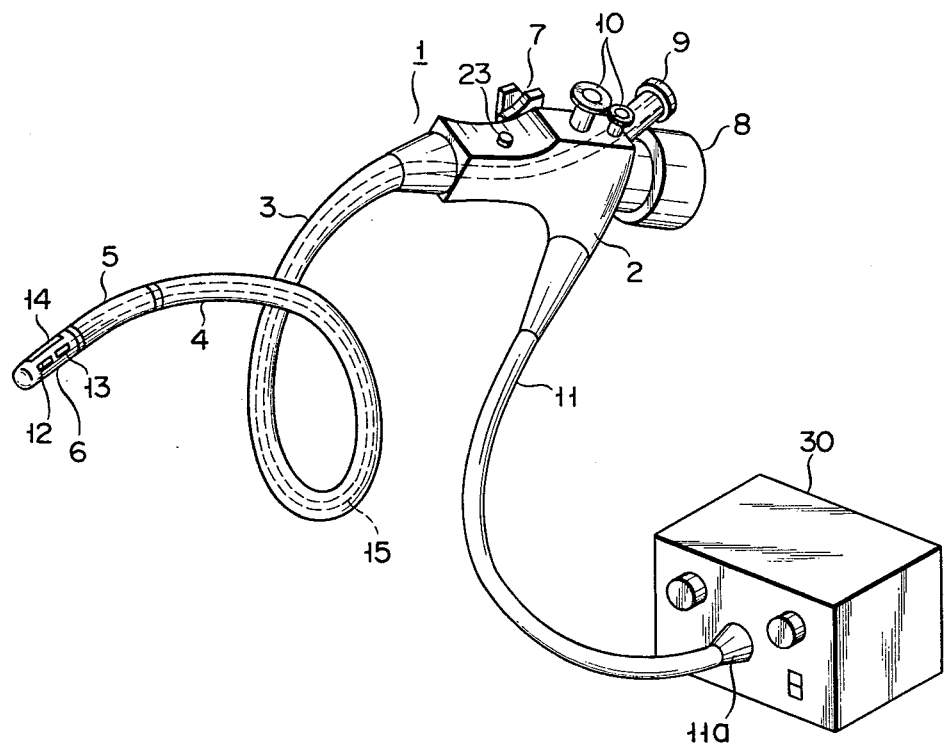
FIG. 1 is a perspective view of an endoscope having a treatment instrument driving device according to one preferred embodiment of the present invention.

In FIG. 1, A side-viewing endoscope 1 is constituted by a control section 2, an insertion section 3, a flexible section 4, a bending section 5 and a distal portion 6. An operation knob 7 for bending and operating the bending section 5 is provided at the side of the control section 2, and an eyepiece 8 is provided at the upper portion. At the control section 2 are provided a forceps channel inlet 9 and suction and air/water feeding buttons 10. A universal cord 11 extends from the control section 2, and a connector 11a provided at the end of the universal cord 11 is connected to a light supply unit 30.

Figure 2:
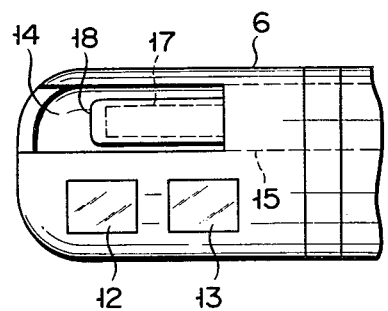
FIG. 2 is a plan view of the distal portion of the endoscope in FIG. 1.

An illumination window 12 and an observation window 13 are provided, as shown in FIG. 2, to be aligned longitudinally at one side of the side surface of the distal portion 6. A forceps closet 14 is formed at the other side of the side surface of the distal portion 6.

The illumination light of the light supply unit 30 is emitted from the illumination window 12 through a light guide (not shown) of the endoscope 1, and the portion illuminated by the illumination light can be observed by the eyepiece 8 through the observation window 13 and an image guide (not shown) of the endoscope 1. A forceps channel 15 passing from the forceps channel inlet 9 provided at the endoscope 1 through the control section 2, the insertion section 3, the flexible section 4 and the bending section 5 to the distal portion 6 is provided in the endoscope 8. The end of the channel 15 communicates with the forceps closet 14. When the treatment instrument, i.e., the forceps 16 is therefore inserted from the forceps channel inlet 9 into the channel 15, the end of the forceps 16 is protruded into the forceps closet 14. A planar forceps raiser 17 is disposed at the back position of the protruded forceps 16 at the forceps closet 14, and the forceps raiser 17 is closely contacted with the open end formed at the rear wall 14a of the forceps closet 14. The forceps raiser 17 is formed of Cu-Zn-Al alloy or Ti-Ni alloy having shape memory effect, and is covered, for example, with an elastic member, such as a rubber 18. The forceps raiser 17 is so composed as to bend to a great extent as the temperature rises. In other words, the crystalline structure of the shape memory alloy forming the forceps raiser 17 becomes mother phase at the high temperature, the forceps raiser 17 thus bends to a great extent, but is plastically deformed at room temperature at which it bends slightly. In the preferred embodiment, the shape memory alloy forming the forceps raiser 17 is so formed that the temperature starting the inverse transformation from the martensite phase to the mother phase becomes higher than the body temperature.

Figure 3:
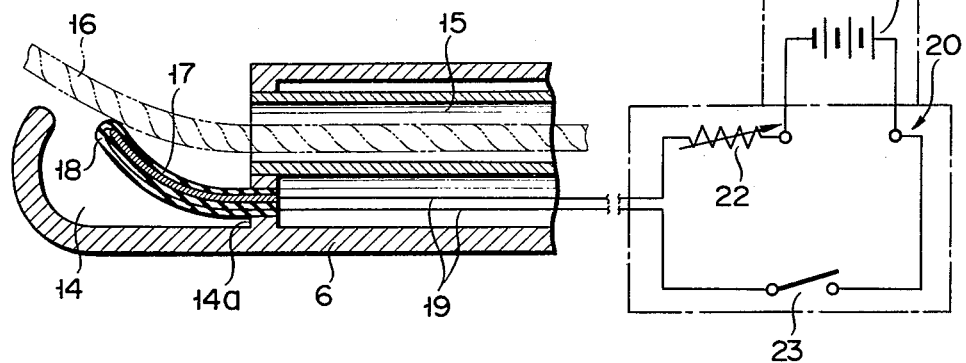
FIG. 3 is a vertical sectional view of the distal portion in FIG. 2.

Lead lines 19 are respectively connected, as shown in FIG. 3, to both the ends of the forcep raiser 17 and are connected to the terminals of a power source 21 through the resistor 22 and the switch 23 of a power unit 20. The resistor 22 and the switch 23 are provided in the control section 2 and the power source 21 is provided in the light supply unit 30. When the connector 11a at the end of the universal cord 11 of the endoscope 1 is connected to the light supply unit 30, power is supplied to the power unit 20.

Figure 4:
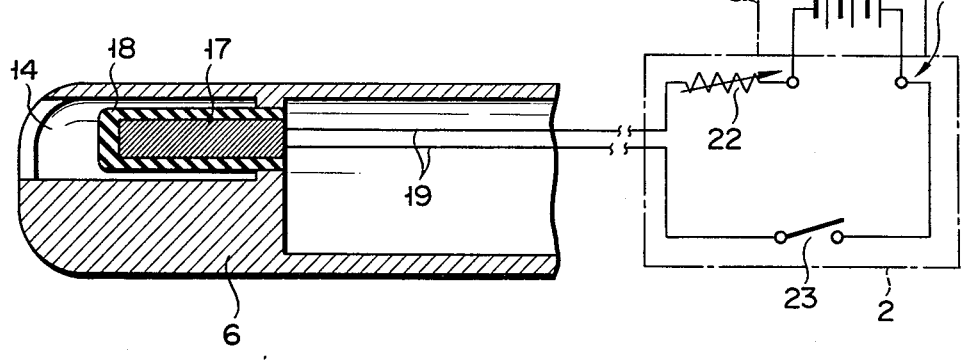
FIG. 4 is a plan sectional view of the distal portion in FIG. 2.
Figure 5:
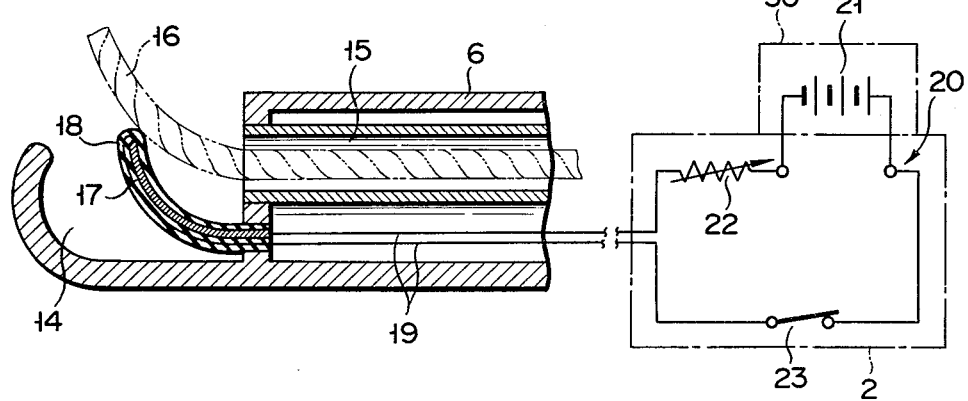
FIG. 5 is a lateral sectional view of the distal portion when the forceps raiser is deformed.

In the forceps raising device thus composed, when the endoscope 1 is inserted into the body cavity, the shape memory alloy of the forceps raiser 17 is in the martensite phase, and the forceps raiser 17 bends slightly. FIG. 4 shows a plan sectional view of the distal portion in FIG. 2. When the forceps 16 is inserted into the forceps channel 15 in this state, the forceps 16 extends in a direction along the axis of the distal portion 6 under the guidance of the forceps raiser 17. When the forceps 16 is displaced and hence raised in this state, the switch 23 is closed to supply a current to the forceps raiser 17. When the current is flowed thus through the forceps raiser 17, the forceps raiser 17 is heated by the Joule heat. When the forceps raiser 17 is thus heated higher than the body temperature, the inverse transformation from the martensite to the mother phase will start, so that the forceps raiser 17 will bend to a great extent as shown in FIG. 5. As the forceps raiser 17 thus bends, the forceps 16 is raised by the forceps raiser 17, and the direction of the forceps 16 is altered. When the switch 23 is opened in this state, the current supply to the forceps raiser 17 is stopped, and the temperature of the forceps raiser 17 is resultantly lowered. When this temperature is decreased to body temperature, the forceps raiser 17 is plastically deformed to the state shown in FIG. 3 while the martensite transformation is being carried out. In this manner, the forceps 16 is returned to the original position. The magnitude of the bending of the forceps raiser 17 can be arbitrarily set by altering the current supplied to the forceps raiser 17 and resultantly varying the temperature of the forceps raiser 17 under the control of the resistor 22.

Another preferred embodiment of the present invention will now be described in more detail with reference to FIGS. 6 and 7. In this embodiment, a forceps raiser 17 is provided in the distal portion 6 of the forward-viewing type endoscope. In the distal portion 6 is engaged a hood 24 protruded from the end face of the distal portion 6. The space formed of the inner peripheral surface of the projection of the hood 24 and the end face 6a of the distal portion 6 becomes a forceps closet 14. An observation window 13 is provided in the distal portion 6, and is optically connected to an image guide fibers 27 through the lenses 26 of an optical system 25. A forceps channel 15 is provided in parallel with the optical system 25 and the image guide fiber 27, and the forceps 16 are inserted into the forceps channel 15. The forceps raiser 17 is mounted at the distal portion 6 in the proximity to the forceps channel 15. In this case, one end of the forceps raiser 17 covered with an elastic member 18 is closely contacted with the distal portion 6 so as not to form a gap with the distal portion 6. The other end of the forceps raiser 17 is inserted into the forceps raiser receiving hole 24a provided at the hood 24. Both ends of the forceps raiser 17 are connected to lead lines 19.

Figure 6:
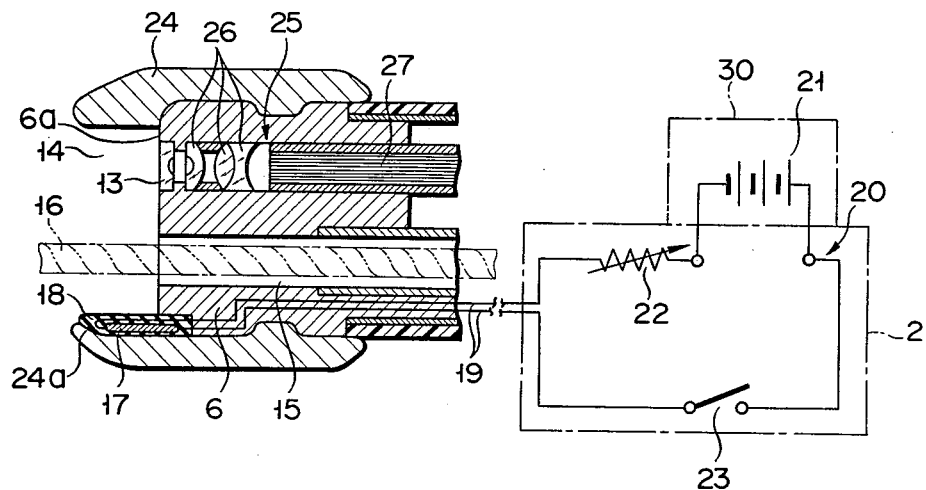
FIG. 6 is a sectional view of the distal portion having the forceps raiser according to another preferred embodiment of the present invention.
Figure 7:
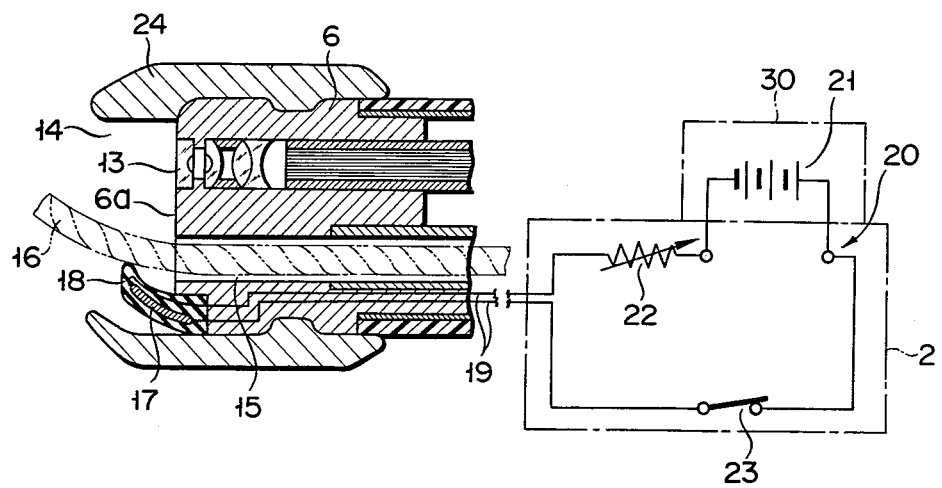
FIG. 7 is a sectional view of the distal portion when the forceps raiser is deformed.

In this embodiment, when the forceps raiser 17 is not energized by the power unit 20, i.e., when the shape memory alloy is in martensite phase, the forceps raiser 17 becomes planar as shown in FIG. 6 and is thus contained in the forceps raiser receiving hole 24a. When the switch 23 is closed to flow a current through the forceps raiser 17 so that the forceps raiser 17 is heated with the result that the shape memory alloy is transferred to the mother phase, the forceps raiser 17 bends to a great extent as shown in FIG. 7 to displace the forceps 16. When the switch 23 is opened so that the temperature of the forceps raiser 17 is decreased to body temperature, the forceps raiser 17 returns to the planar state. The bending degree of the forceps raiser 17 is also controlled in this embodiment by altering the resistor 22.

According to the present invention as described above, the forceps raiser is so provided at the forceps closet of the distal portion of the endoscope as not to form a gap with the wall of the forceps closet. It is formed of the shape memory alloy which alters its shape in response to the temperature. The power unit is connected to the forceps raiser formed of the shape memory alloy, and the temperature of the forceps raiser is adjusted by controlling the current from the power unit to the forceps raiser. The forceps raiser is thus displaced, and the position of the forceps can also be displaced. Since the forceps raising device thus composed does not substantially have a mechanical driving unit, its structure simple and small in size. Furthermore, no gap is formed through which contaminants can be introduced in the structure. Therefore, as the forceps raiser can operate without any problem, it is not necessary to increase the diameter of the distal portion it remains sanitary.

The above embodiments have been described with the forceps raising device raising the forceps, but the present invention may also be applied to treatment instruments other than the forceps.

What is claimed is:

1. In an endoscope having a control section, an insertion section with a proximal and distal end, a treatment instrument, a treatment instrument closet, and an instrument channel, the improvement comprising:
    a treatment instrument driving device comprising:
        a treatment driving member protruding into said treatment instrument closet provided in said distal portion of said endoscope, and adjacent to said channel provided in said endoscope in which is inserted detachably a treatment instrument, said treatment driving member being formed of a shape memory alloy varying in shape in accordance with temperature, and
        means connected to said treatment driving member for supplying a current to said treatment driving member to raise the temperature of said treatment driving member, thereby displacing the treatment instrument according to the varying of the shape of said treatment driving member.

2. The treatment instrument driving device according to claim 1, wherein said treatment instrument is a forceps and said treatment driving member is formed of a shape memory alloy plate and an elastic member covered on the plate.

3. The treatment instrument driving device according to claim 1, wherein said current supplying means comprises lead wire means inserted into said endoscope and connected to said treatment driving member, and means connected to said treatment driving member through the lead wire means for controlling a current from a power source.

4. The treatment instrument driving device according to claim 3, wherein said current controlling means comprises a switch connected between the power source and the lead wire means, and a variable resistor.

5. The treatment instrument driving device according to claim 4, wherein said current controlling means is provided in the control section of said endoscope, and said power source is provided in a light supply unit.

6. The treatment instrument driving device according to claim 1, 2 or 3, wherein said endoscope is a side-viewing endoscope having an observation window and an illumination window as well as forceps closed at the side face of the distal portion.

7. The treatment instrument driving device according to claim 1, 2 or 3, wherein said endoscope is a forward-viewing endoscope having a forceps closet at the forward of the distal portion and capable of observation in the forward direction.

* * * * *